(12) United States Patent
Selck et al.

(10) Patent No.: US 11,443,181 B2
(45) Date of Patent: Sep. 13, 2022

(54) APPARATUS AND METHOD FOR CHARACTERIZATION OF SYNTHETIC ORGANISMS

(71) Applicant: NORTHROP GRUMMAN SYSTEMS CORPORATION, Falls Church, VA (US)

(72) Inventors: David A. Selck, Sterling, VA (US); Om Prakash, II, McLean, VA (US); H. Morgan Crafts, Jr., Oakton, VA (US); Sam S. Shekar, Potomac, MD (US)

(73) Assignee: PERATON INC., Herndon, VA (US)

( * ) Notice: Subject to any disclaimer, the term of this patent is extended or adjusted under 35 U.S.C. 154(b) by 1123 days.

(21) Appl. No.: 16/010,637

(22) Filed: Jun. 18, 2018

(65) Prior Publication Data

US 2019/0385053 A1    Dec. 19, 2019

(51) Int. Cl.
| | |
|---|---|
| *G06N 3/08* | (2006.01) |
| *G16B 40/00* | (2019.01) |
| *G16B 40/20* | (2019.01) |
| *G16B 20/00* | (2019.01) |
| *G06N 3/04* | (2006.01) |

(52) U.S. Cl.
CPC ............. *G06N 3/08* (2013.01); *G06N 3/0445* (2013.01); *G06N 3/0454* (2013.01); *G16B 20/00* (2019.02); *G16B 40/00* (2019.02); *G16B 40/20* (2019.02)

(58) Field of Classification Search
CPC ...... G06N 3/08; G06N 3/0445; G06N 3/0454; G16B 20/00; G16B 40/00; G16B 40/20
See application file for complete search history.

(56) References Cited

U.S. PATENT DOCUMENTS

2016/0364522 A1\* 12/2016 Frey ........................ G16B 20/20
2020/0302224 A1\* 9/2020 Jaganathan ............ G06N 3/084

\* cited by examiner

*Primary Examiner* — Diane D Mizrahi
(74) *Attorney, Agent, or Firm* — Burr & Forman, LLP

(57) ABSTRACT

A system for classifying an origin of genomic sequence data may include a training database comprising sample data including first samples corresponding to sequences of natural origin and second samples corresponding to sequences of synthetic origin, and a classifier comprising a genomic classification module. The genomic classification module may be trained via machine learning on the first and second samples. The genomic classification module may be configured to receive genomic sequence data of any read length and determine a classification output indicating whether the genomic sequence data has a natural origin or synthetic origin.

20 Claims, 4 Drawing Sheets

APPARATUS AND METHOD FOR CHARACTERIZATION OF SYNTHETIC ORGANISMS

TECHNICAL FIELD

Example embodiments generally relate to classification of genomic material and, in particular, relate to a system for analyzing genomic material to determine whether the genomic material has a synthetic or natural source and, in some cases, enabling further characterization of various synthetic materials.

BACKGROUND

Deoxyribonucleic acid (DNA) is a chain of nucleotides that carry genetic instructions that are essential for all known forms of life. Although naturally occurring DNA has been studied extensively since its discovery in the late $19^{th}$ century, the tools for studying and manipulating DNA began to advance rapidly in the second half of the $20^{th}$ century, and early part of the $21^{st}$ century. These tools have given rise to the ability to create artificial genes through gene synthesis thereby resulting in synthetic DNA. Synthetic DNA sequences are sequences of nucleotides that have not been derived from living material through genetic inheritance, but instead have been designed in silico, manufactured using any of a variety of methods. Some of these methods include the purchase of genetic material through a variety of commercial suppliers for insertion of such material into a host cell. The host cell may then be provided with capabilities that it would otherwise not have. This process may be used in a variety of industries to produce high value chemicals and materials in a cost effective, scalable and precise manner.

Given that synthetic DNA sequences can have very positive effects, the drive to advance the field of synthetic biology continues to result in an expansion of the tool sets used to create synthetic DNA. However, the development and application of synthetic DNA could also potentially result in the accidental or intentional creation of powerful bio weapons. As the field of synthetic biology matures and becomes more prevalent across the global scientific/business spectrum, the knowledge, skills and technology required for modifying genomes will become more widely accessible across populations, cheaper/easier to develop and more broadly deployable by organizations and even individual actors. The potential for its accidental or intentional misuse in a harmful capacity could therefore also increase (on both a symmetric and asymmetric basis). If such misuse were to occur, it could present serious and broad implications for human/animal populations. In spite of this threat, as the field of synthetic biology matures, and the technology required for modifying genomes becomes cheaper and easier to use, the chance that some actor uses these tools for destructive purposes also increases. For example, synthetic DNA could be used to create powerful bioweapons either through bioterror or even bioerror. In spite of this threat, there is currently no analytic framework with which one can determine the history of a genomic sequence to determine whether an organism was created through natural or laboratorial means. Accordingly, it may be desirable to provide tools for rapid decisions regarding whether particular genes have been created through natural or synthetic means.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

BRIEF SUMMARY OF SOME EXAMPLES

Figure 1:
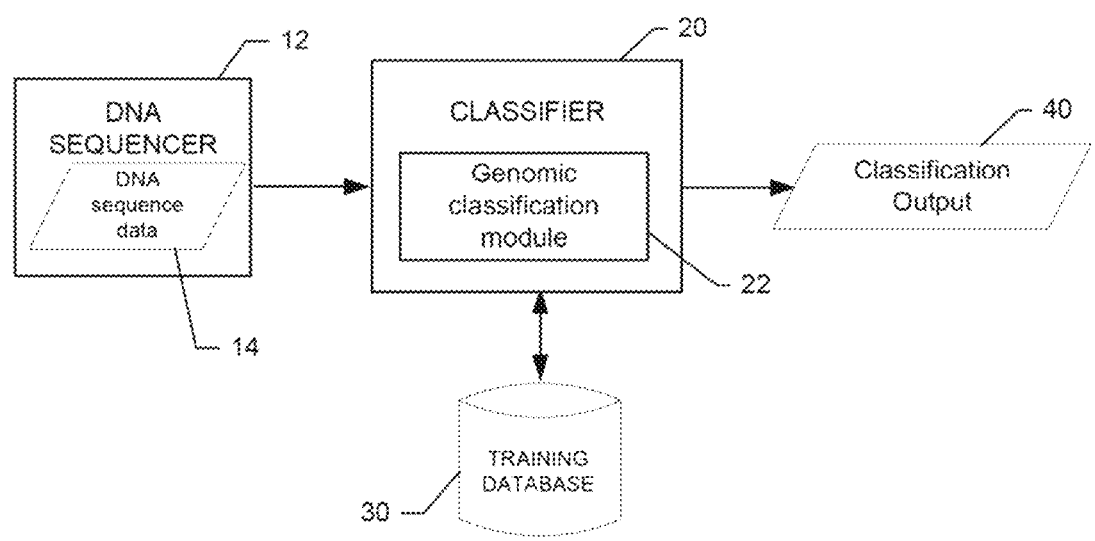
FIG. 1 illustrates a functional block diagram of a system that may be useful in connection with generating determinations regarding whether DNA sequence data is of natural or synthetic origin according to an example embodiment.

In accordance with an example embodiment, a method for classifying an origin of genomic sequence data may be provided. The method may include training a genomic classification module of a classifier via machine learning on first samples corresponding to sequences of natural origin and second samples corresponding to sequences of synthetic origin, receiving raw or processed genomic sequence data of any read length at the classifier, and determining a classification output indicating whether the raw or processed genomic sequence data has a natural origin or synthetic origin via the genomic classification module.

In accordance with another example embodiment, a system for classifying an origin of genomic sequence data may be provided. The system may include a training database comprising sample data including first samples corresponding to sequences of natural origin and second samples corresponding to sequences of synthetic origin, and a classifier comprising a genomic classification module. The genomic classification module may be trained via machine learning on the first and second samples. The genomic classification module may be configured to receive raw or processed genomic sequence data of any read length and determine a classification output indicating whether the raw or processed genomic sequence data has a natural origin or synthetic origin.

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. Furthermore, as used herein, the term "or" is to be interpreted as a logical operator that results in true whenever one or more of its operands are true. As used herein, the terms "data," "content," "information" and similar terms may be used interchangeably to refer to data capable of being transmitted, received and/or stored in accordance with example embodiments. As used herein, operable coupling should be understood to relate to direct or indirect connection that, in either case, enables functional interconnection of components that are operably coupled to each other.

As used herein, the terms "component," "module," and the like are intended to include a computer-related entity, such as but not limited to hardware, firmware, or a combination of hardware and software. For example, a component or module may be, but is not limited to being, a process running on a processor, a processor, an object, an executable, a thread of execution, and/or a computer. By way of example, both an application running on a computing device and/or the computing device can be a component or module. One or more components or modules can reside within a process and/or thread of execution and a component/module may be localized on one computer and/or distributed between two or more computers. In addition, these components can execute from various computer readable media having various data structures stored thereon. The components may communicate by way of local and/or remote processes such as in accordance with a signal having one or more data packets, such as data from one component/module interacting with another component/module in a local system, distributed system, and/or across a network such as the Internet with other systems by way of the signal. Each respective component/module may perform one or more functions that will be described in greater detail herein. However, it should be appreciated that although this example is described in terms of separate modules corresponding to various functions performed, some examples may not necessarily utilize modular architectures for employment of the respective different functions. Thus, for example, code may be shared between different modules, or the processing circuitry itself may be configured to perform all of the functions described as being associated with the components/modules described herein. Furthermore, in the context of this disclosure, the term "module" should not be understood as a nonce word to identify any generic means for performing functionalities of the respective modules. Instead, the term "module" should be understood to be a modular component that is specifically configured in, or can be operably coupled to, the processing circuitry to modify the behavior and/or capability of the processing circuitry based on the hardware and/or software that is added to or otherwise operably coupled to the processing circuitry to configure the processing circuitry accordingly.

Some example embodiments may enable a determination to be made regarding whether a particular genomic sequence was derived using synthetic or natural means. In this regard, some example embodiments may allow fragments of genomic material to be rapidly analyzed to determine their origin. In some cases, a further analysis may also indicate more detailed characteristics of the genomic material to, for example, identify threats and assist in determining appropriate responses to any identified threats. Since example embodiments can work on raw sequence information, the system associated therewith can be modularized for use with any sequencing platform, and can easily be integrated into any gene sequencing pipeline. In this regard, FIG. 1 illustrates an example of a system 10 for classifying genomic sequence data in accordance with an example embodiment.

Referring now to FIG. 1, the system 10 may include a DNA sequencer 12 that is configured to generate DNA sequence data 14. The DNA sequencer 12 may be any known or future machine that is configured to generate DNA sequence data 14, and the type of such machine is outside the scope of the present invention except that it should be noted that one unique aspect of example embodiments is that they work with any DNA sequencer. As such, the DNA sequence data 14 may be raw DNA sequence data gathered at any read length that is generated by the DNA sequencer 12. However, example embodiments do not only work on raw DNA sequenced data. In fact, example embodiments may also work on sequences that have been processed through any known methods including alignment and assembly as mentioned below. In either case, the raw or processed DNA sequence data may have any read length. Some examples of the DNA sequencer 12 may include, without limitation, those made by companies such as Illumina, Life Technologies, Thermo Fisher Scientific, Beckman Coulter, Pacific Biosciences, Oxford Nanopore, Roche, and others under various model and brand names.

The various models and brands noted above as potential examples of the DNA sequencer 12 have widely varying read lengths. Thus, for example, the DNA sequence data 14 resulting from different machines could also have read lengths that vary from 50 base pairs (bp) to 14,000 bp. As noted above, and as will be discussed below in greater detail, one of the advantages of example embodiments is the ability to process the DNA sequence data 14 regardless of the read length of such data. The flexibility thereby provided using example embodiments, enables raw sequence data to be processed very quickly to produce both timely and accurate results.

The DNA sequence data 14 is then fed into a classifier 20 of an example embodiment as described in greater detail below. The classifier 20 may include a genomic classification module 22 that may be trained to perform desired classification tasks. The training may be accomplished using a training database 30 that may include a large amount of both synthetic and natural data that can be retrieved from a variety of public sources (e.g., National Institutes of Health, National Center for Biotechnology Information, AddGene, etc.) or proprietary/private sources. The training database 30 may be embodied as a library of motif level sequences associated with known natural and synthetic organisms. In some cases, the training database 30 may include a library for all natural and all synthetic organisms that are known. However, in other cases, the training database 30 may be specific to a type of organism based on the type of organism suspected to be associated with the DNA sequence data 14. Thus, for example, if the DNA sequence data 14 is for a particular strain of corn, the training database 30 may be specific at any desirable level in order to include corn data. In this regard, for example, the training database 30 could include all seeds, all grain seeds, or all corn seeds, depending upon the situation and/or the data sources that are available. Different databases could then be substituted to allow different classifications to be accomplished so that one instance of the classifier 20 can be reconfigured to make classifications of any of a number of different desirable types of organisms. The reconfiguration is accomplished by retraining algorithms of the genomic classification module 22 on respective different instances of the training database 30. However, as noted above, in some cases, the training database 30 could be broadly applicable to many different types of organisms as well.

The training database 30 may therefore act as a feature library for any of various biological functions of known organisms of a particular type at any desirable level of granularity that is desired for the training database 30. In this regard, for example, the training database 30 may include one or more sets of training data that can be used to facilitate machine learning algorithms that effectively train the genomic classification module 22 to perform the types of classification that the training database 30 includes information on. In an example embodiment, the training database 30 may include genomic data defining all or portions of the genomes of various known synthetic and natural organisms segmented at the motif level. The training database 30 may therefore enable the genomic classification module 22 to be configured to compare the DNA sequence data 14 (having any read length) to models built within the genomic classification module 22 also at the motif level and therefore having various sizes. Based on the determination of matches between the DNA sequence data 14 and segments of training data generated from the training database 30, the genomic classification module 22 may be able to distinguish between natural and synthetic origins for any given DNA sequence data 14 that is entered. In this regard, for example, if the DNA sequence data 14 includes sequences that only match with natural sequences from the training database 30, the DNA sequence data 14 may be determined to be of natural origin. However, if the DNA sequence data 14 includes some segments that match with synthetic sequences, then the DNA sequence data 14 may be determined to be of synthetic origin. Accordingly, in some cases, the classification output 40 may include only a determination regarding whether the DNA sequence data 14 that was inserted has a natural or synthetic origin based on the comparison. However, the classification output 40 may, in some cases, also include a confidence score indicating a confidence level associated with the determination regarding origin of the DNA sequence data 14.

The confidence level may be determined based on a number of segments matched, a degree to which matching occurs, a length of the matched segment(s), a quality score (e.g., measurement of the likelihood that the sequencer made the correct base call) associated with data generated by the sequencer, etc. In this regard, the confidence may increase with an increased number of matches, with a higher percentage of matching, with a longer sequence that matches, or with a higher quality score generated by the sequencer. However, as the genomic classification module 22 gains more experience in the machine learning process, it may also be possible to attach higher confidence to certain matches based on the rarity of occurrence of particular segments or sequences that have matched as well. Thus, the confidence level may include statistical computations that can further be based on (and improve with) experiential factors. In some cases sequences and larger complexes of motifs may also point to synthetic and/or natural sequences. Thus, the confidence level may also be dependent at least to some degree on the motifs or structural patterns of the DNA sequence data 14.

Figure 2:
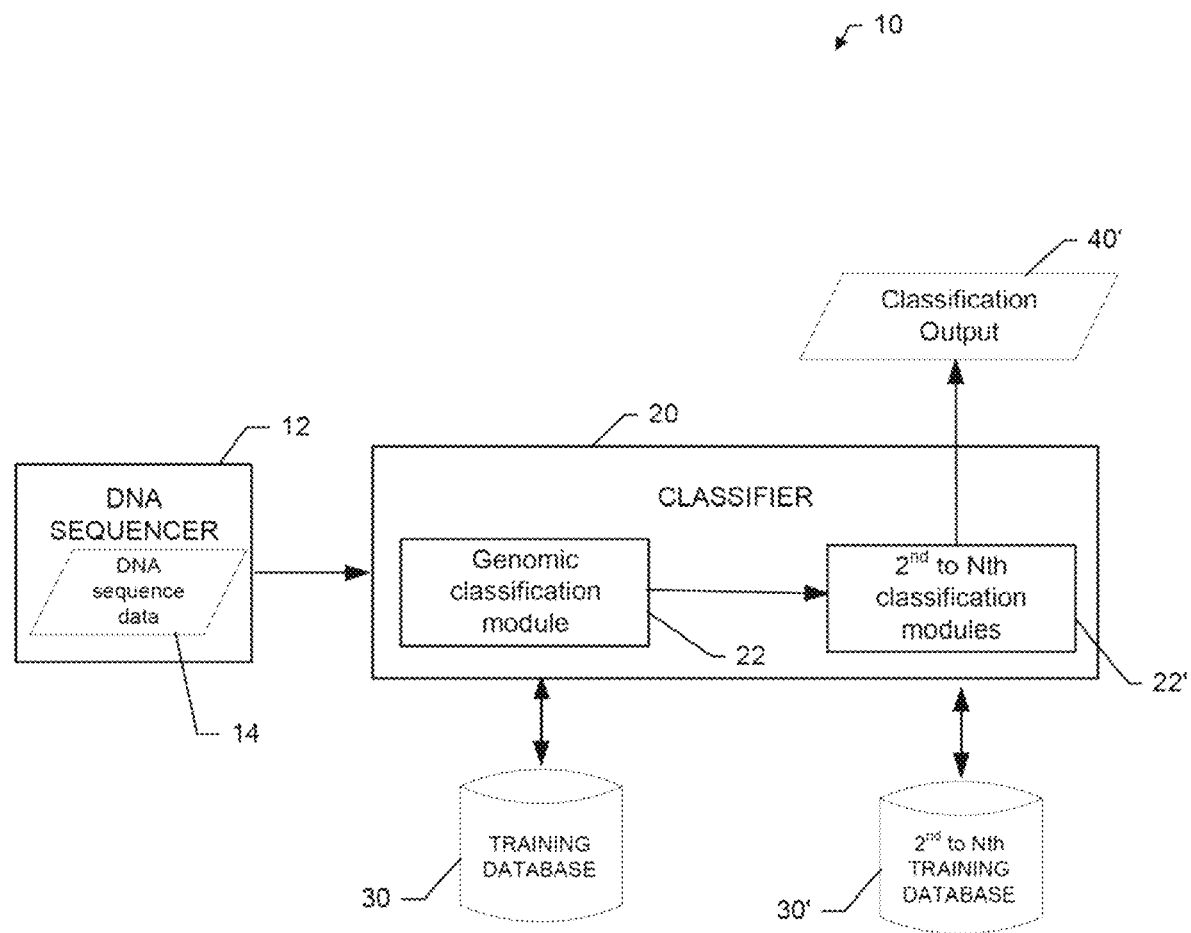
FIG. 2 illustrates a functional block diagram of the system configured to perform additional determinations regarding attributes or characteristics of DNA sequence data according to an example embodiment.

In some examples, the classifier 20 may be configured to generate the classification output 40 only indicating the origin of the DNA sequence data 14 (e.g., natural or synthetic, with or without a confidence score), and such output may be deemed sufficient. However, in other cases, it may be desirable to configure the classifier 20 to perform additional classification efforts for those samples that have been determined to have synthetic origin. In such examples, the classifier 20 may be configured to include one or more additional classification modules that may each be trained to make the corresponding determinations desired for each use case. FIG. 2 illustrates an example structure that may be employed for such additional classification capabilities.

Referring now to FIG. 2, it can be appreciated that the classifier 20 may be expanded to include any number of additional classification modules (e.g., $2^{nd}$ to Nth classification modules 22'), each of which may have a corresponding set of training databases (e.g., $2^{nd}$ to Nth training databases 30') associated therewith. The $2^{nd}$ to Nth training databases 30' may be used to train the respective ones of the $2^{nd}$ to Nth classification modules 22' to perform the corresponding comparisons and determinations regarding specific different attributes or characteristics for which classification is desired. Accordingly, for example, the $2^{nd}$ to Nth classification modules 22' may each be specific to a particular attribute or characteristic, so that the output classification 40' may include additional information specific to the corresponding attribute(s) or characteristic(s) for which the $2^{nd}$ to Nth classification modules 22' are configured to make determinations. The attributes or characteristics that the $2^{nd}$ to Nth training databases 30' may be specific to could include, for example, authorship, function, harmfulness, etc.

In this regard, for example, a database may include a plurality of known synthetic DNA sequences with known provenance or authorship. The corresponding classification module for the database may be trained to recognize sequences within the DNA sequence data 14 that is input into the system 10. Thus, when matches occur, a provenance or authorship determination may be made (sometimes also with a corresponding confidence level) for the DNA sequence data 14 in the form of the output classification 40' providing an indication that the DNA sequence data 14 has a synthetic origin and providing an indication of the identity of the origin or at least an identity of an author of one or more segments of the DNA sequence data 14 (since more than one known author may have contributed to different portions). A similar process may also or alternatively be performed for portions or segments of the DNA sequence data 14 with respect to function, and any number of other attributes and/or characteristics of interest.

In the example of FIG. 2, the genomic classification module 22 may operate to make a determination regarding synthetic/natural origin of the DNA sequence data 14. If a natural origin is determined, the classification output 40' may be generated to indicate as much, and the process may stop. However, if the DNA sequence data 14 is determined to have synthetic origin, then further analysis to determine additional attributes, features or characteristics may be accomplished by the $2^{nd}$ to Nth classification modules 22'. The classification output 40' may therefore include corresponding determinations for any or all of the additional attributes, features or characteristics.

Figure 3:
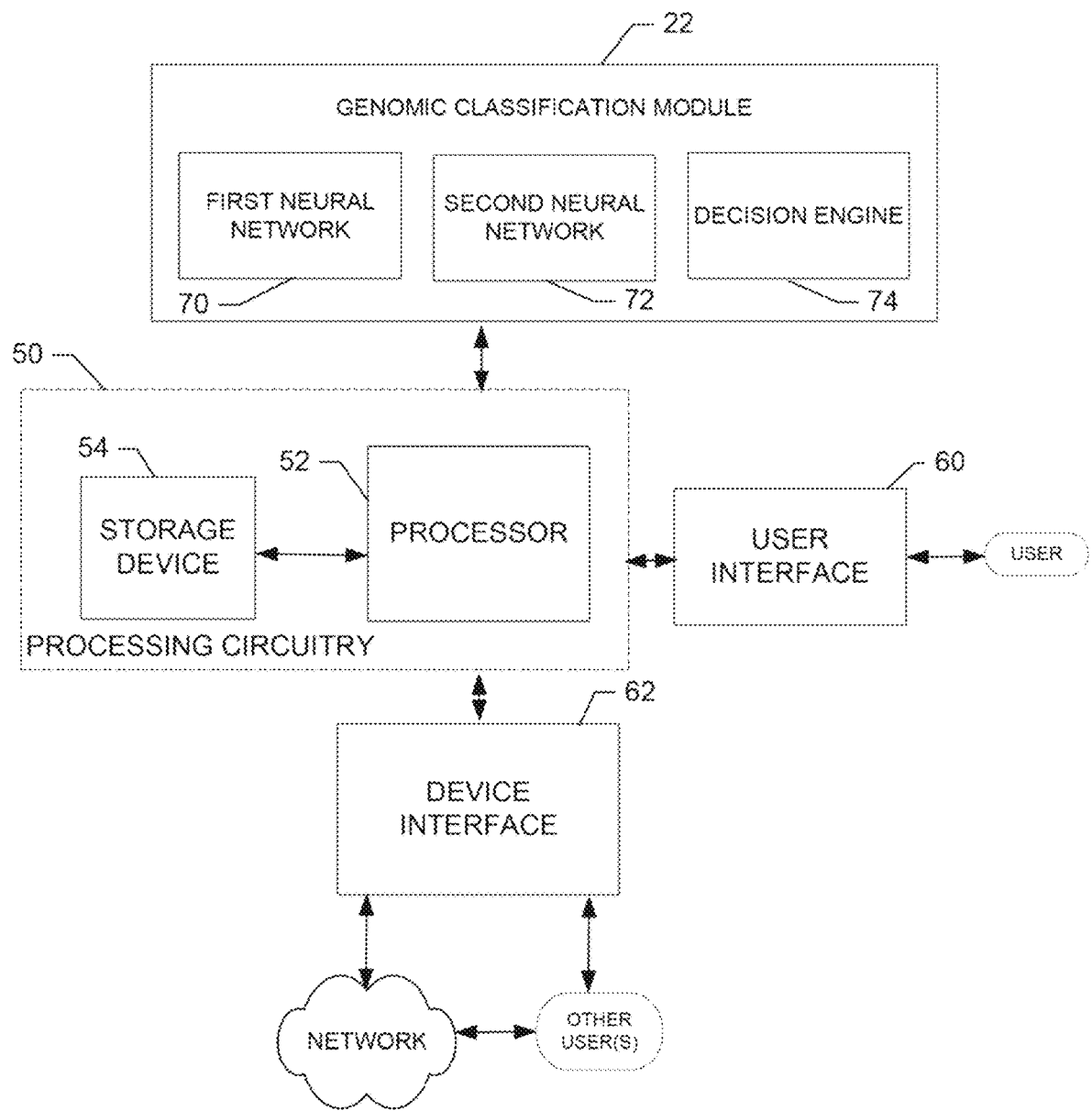
FIG. 3 illustrates a block diagram of a classifier in accordance with an example embodiment.

An example embodiment of the invention will now be described with reference to FIG. 3. FIG. 3 shows certain components of the classifier 20 according to an example embodiment. In an example embodiment, the classifier 20 may include or otherwise be in communication with processing circuitry 50 that is configured to perform data processing, application execution and other processing and management services according to an example embodiment of the present invention. In one embodiment, the processing circuitry 50 may include a storage device 54 and a processor 52 that may be in communication with or otherwise control a user interface 60 and a device interface 62. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation or even one of various mobile computing devices. In situations where the processing circuitry 50 is embodied as a server or at a remotely located computing device, the user interface 60 may be disposed at another device that may be in communication with the processing circuitry 50 via the device interface 62 and/or a network.

The user interface 60 may be in communication with the processing circuitry 50 to receive an indication of a user input at the user interface 60 and/or to provide an audible, visual, mechanical or other output to the user. As such, the user interface 60 may include, for example, a keyboard, a mouse, a joystick, a display, a touch screen, a microphone, a speaker, a cell phone, or other input/output mechanisms. In embodiments where the apparatus is embodied at a server or other network entity, the user interface 60 may be limited or even eliminated in some cases. Alternatively, as indicated above, the user interface 60 may be remotely located.

The device interface 62 may include one or more interface mechanisms for enabling communication with other devices and/or networks. In some cases, the device interface 62 may be any means such as a device or circuitry embodied in either hardware, software, or a combination of hardware and software that is configured to receive and/or transmit data from/to a network and/or any other device or module in communication with the processing circuitry 50. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an example embodiment, the storage device 54 may include one or more non-transitory storage or memory devices such as, for example, volatile and/or non-volatile memory that may be either fixed or removable. The storage device 54 may be configured to store information, data, applications, instructions or the like for enabling the apparatus to carry out various functions in accordance with example embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases that may store a variety of files, contents or data sets. Among the contents of the storage device 54, applications may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an example embodiment, the processor 52 (or the processing circuitry 50) may be embodied as, include or otherwise control the genomic classification module 22, which may be any means such as a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the genomic classification module 22 as described below.

The genomic classification module 22 may include tools to facilitate the training of algorithms to identify the origin and, in some cases, the attributes or characteristics of raw DNA sequence data (e.g., the DNA sequence data 14). As discussed above, the read lengths that result from a DNA sequencer can vary, but the genomic classification module 22 is configured to handle the different read lengths without any other pre-processing. The changes that distinguish a natural gene from a synthetic gene can be subtle changes that may occur over short length scales. Furthermore, the changes may be asserted in ways that include, for example silencing restriction sites, inserting canonical enhancers and promoters, codon optimization of protein coding regions, etc. In other cases, subtle indicators may be observed at moderately longer length scales by interrogating features such as the organization of the DNA circuit and the specific elements that are chosen. There are also even broader genomic-length scale changes that can be captured including things such as off-target effects of CRISPR-Cas9 editing. Capturing a combination of length scale effects may be very helpful in providing the best possible approximation of the genetic patronage of an interrogated sequence.

There may be a variety of mechanisms by which to capture the effects described above. However, some example embodiments may take the approach of providing two different neural networks as part of the genomic classification module 22. In particular, for example, the two different neural networks may be configured to operate at different length scales (i.e., one short and one long) in order to provide good performance for detection of any of the effects described above (or others) regardless of the length scale with which each such effect is primarily associated. Accordingly, as shown in FIG. 3, the genomic classification module 22 may include a first neural network 70 and a second neural network 72. Each of the first and second neural networks 70 and 72 may be configured to perform better over respective different length scales, or for particular other sets of data. For example, the first neural network 70 may be configured to have better performance (i.e., better ability to find matches) over shorter length scales, and the second neural network 72 may be configured to have better performance over longer length scales. In some examples, the first neural network 70 may be a convolutional neural network (CNN) and the second neural network 72 may be a recurrent neural network (RNN). However, any combination of neural networks or even other types of networks could be substitutes in various example embodiments. For example, multiple CNNs that are each tailored to different length scales could be used in some cases. Other combinations are also possible.

CNNs are well regarded, modern, and well-grounded tools that can be used to pinpoint and highlight common effects observed over a specific and pre-determined length scale. While CNNs have gained significant popularity due to their ability to analyze imagery, CNNs have also shown promise as compelling solutions in motif discovery of genomic data. RNNs, and specifically those architected with long short-term memory nodes, on the other hand, may be suited to capturing long-range effects. The capability of RNNs to capture longer scale effects has been observed in fields such as language translation, predicting protein folding and structure, and other areas. Thus, it is also expected that RNNs may be well suited to detect matches in compared sequences over long length scales in a motif level comparison context. However, it should be appreciated that the specific nodes mentioned herein are merely examples of nodes that may be used in some cases, and other options that are developed in the future may not only work but, in some cases, could even work better than those that are specifically discussed herein.

In an example embodiment, the RNN and CNN can be used in combination with each other by the genomic classification module 22. In particular, in some cases the RNN and CNN may be used in series, with the output of one providing the input to the other. For example, the output of the first neural network 70 (e.g., the CNN) may provide the input to the second neural network 72 (e.g., the RNN). By combining the output of the RNN with a genome wide search may include genome-scale effects such as off-target effects, and the results can then be fed into a final classification algorithm (e.g., decision engine 74) that is configured to make final calls regarding classifications as either the classification output 40 or 40'. However, it should be appreciated that other frameworks including a variety of other machine learning techniques and network types could be employed in other embodiments. Moreover, the characteristics of the networks and techniques employed can be tailored to the particular purpose or stated goal of discerning synthetic from natural sequences, and of determining specific attributes or characteristics of the synthetic sequences that have been identified.

As an example, a combination of a CNN and an RNN may be used to analyze any sequence length without requiring null characters (that would otherwise be necessary to enable analysis due to neural networks normally having a fixed input vector size). This may be accomplished by taking an input sequence and breaking it up into N number of smaller sequences of size Y. These sequences can also be overlapping in order to ensure the best "coverage" of the input sequence. All of the N sequences may then be fed sequentially into a CNN crafted to specifically analyze sequences of size Y. The outputs of the CNN may then be fed sequentially into an RNN, which has been designed to collate an unknown number of input sequences into an answer. This answer could either be a single answer, which determines the synthetic/natural nature of the original input sequence, or, it could give an answer which denotes the likelihood that different sub-regions of the input sequence are either natural or synthetic in nature. This could be important since, in a large input sequence, it is possible that a splice point may be in the middle of a sequence to be analyzed and some of the sequence may be natural and some of the sequence may be synthetic. The power of this method, as opposed to just analyzing each sub-region as a standalone sequence, is that a better answer can be obtained by the incorporation of more input data. In other words, a better confidence score can be obtained by looking at the entire input sequence as a whole (using the combination of the CNN and RNN) as opposed to small and individual input sequences.

Another possible architecture that is similar may, instead of having two CNNs of differing lengths, have N CNNs which are setup to analyze input sequences of differing lengths. Therefore, if it was desirable to be able to analyze sequences as small as 50 bp and as long as 15000 bp. One may setup a set of CNNs which are architected to analyze sequences at 100 bp intervals, i.e. 100, 200, 300 . . . 14800, 14900, 15000. Any input sequence would then just be rounded up in length to the nearest available size, and null characters would be inserted at the beginning and end of the sequence such that the real sequence is centered around null values. This sequence would then be analyzed and an answer arrived at. This method would be able to provide a single answer as to the synthetic/natural nature of an input sequence of varying input size.

As noted above, the DNA sequence data 14 can be either raw sequence information or processed sequence information that can have any of a number of read lengths. The fact that the genomic classification module 22 is configured to include first and second neural networks 70 and 72 that are configured to perform better over different length scales ensures that the DNA sequencer 12 could be any sequencing platform such that the classifier 20 can be easily integrated into any gene sequencing analysis pipeline. Modularization of the system 10 may therefore enable an application programming interface (API) to be defined that enables the classifier 20 to be prepended to a variety of different analysis pipelines and tools to extend the usefulness of the system 10. Having a modular structure may also enable deployment of the system 10 with a variety of post-classification packages to perform analyses such as determining a probable author or function of discovered synthetic sequences as described above. For example, both long-range and motif level effects may each have implications in determining the author or a sequence as different people may prefer different gene circuit architectures and elements. Thus, theoretically, the decision engine 74 could be changed, tuned, configured, or otherwise tailored to the particular classification decision that is being made. Modules may also be developed (e.g., using the methodologies described above) for other purposes using the general outline described above. Thus, an initial stage of determining natural versus synthetic origin could be followed by additional stages or layers that are modular in nature and that are tailored to specific classification tasks of interest. As such, any number of different modules could be added or subtracted to the system 10 in order to increase the capabilities of the system 10. In some cases, modules could be added before or after the synthetic/natural classification module to either enhance granularity of determinations (e.g., if added after and focused on a particular attribute) or to decrease computational load (e.g., if added before and focused on finding sequences more likely to achieve matches or otherwise reduce load on the neural networks or other components).

The training data of the training database 30 may include, for example, large numbers of samples or segments of DNA sequences and corresponding assignments of such samples or segments to particular classifications, attributes or characteristics. Thus, for example, the training data may include vast numbers of samples of DNA sequences with corresponding assignments as being either natural or synthetic DNA sequences. Of course, other databases may substitute other classifications relating to authorship, harmfulness, function, etc. When the first and second neural networks 70 and 72 have been trained using the training data associated with the training database 30, each of the first and second neural networks 70 and 72 will be configured to, over the respective length scales associated therewith, attempt to learn the function or functions that find an optimal solution from the sequence data associated therewith to the classifications or attributes assigned to the sequence data. In the example above, the neural networks attempt to learn the optimal function or functions from the sample data that result in the corresponding assigned classification (e.g., either natural or synthetic). The learned function or functions are then applied to the DNA sequence data 14 to enable the classifier 20 (i.e., via the genomic classification module 22 and thereby also the first and second neural networks 70 and 72) to make an assignment of a particular classification (e.g., natural or synthetic) to the DNA sequence data 14 (or to particular segments or portions thereof). The classification output could be a binary output (e.g., natural or synthetic), or could be rated or scored output that can be compared to a scale that includes the determinations (e.g., natural or synthetic) such that the rating or score is compared to the scale to make a final determination regarding the classification.

In some embodiments, a separate classification output may be generated by each of the first and second neural networks 70 and 72. The decision engine 74 may then be configured to take each of the classification outputs and make a final determination or final classification (i.e., the classification output 40 or 40') for the DNA sequence data 14. The decision engine 74 can be configured with weighting factors or other guidance to direct the combining of inputs from each of the first and second neural networks 70 and 72. However, in other cases (e.g., when the output of the first neural network 70 feeds directly into the input of the second neural network 72), the decision engine 74 may simply take the combined output from the first and second neural networks 70 and 72 and utilize programmed guidance (e.g., employing the rating/scoring paradigm discussed above or other guidance) to generate the output classification. Moreover, in some cases, the decision engine 74 may be configured to determine the confidence level and assign the same to the classification output 40 or 40' based on the criteria discussed above. In some cases, the decision engine 74 may also provide some or all classification outputs 40 or 40' to a user (e.g., via the user interface 60) for evaluation for addition to the training database 30 (or 30'). In this regard, for example, if the confidence level is above a certain threshold, the corresponding classification output may have enough confidence associated therewith to merit investigation by an expert to enable the corresponding DNA sequence data 14 and its classification output 40 to be added as a sample in the training database 30.

Of course, all of the discussion above relating to the genomic classification module 22 and its operation may be duplicated in the $2^{nd}$ to Nth classification modules 22' except with respect to corresponding other attributes, features, characteristics, etc., instead of the natural/synthetic determination. As such, each of the $2^{nd}$ to Nth classification modules 22' may also include corresponding instances of the first and second neural networks 70 and 72 trained with respective ones of the $2^{nd}$ to Nth training databases 30'. Each of the $2^{nd}$ to Nth classification modules 22' may also include a corresponding instance of a decision engine 74 to combine or make a classification output determination regarding the combined outputs from the corresponding instances of the first and second neural networks 70 and 72.

Current solutions for determining whether a gene is synthetic or natural are fragmented, are generally unassisted by purpose-driven software, and require key experts to perform interpretation. It is also not clear that expert bioinformaticians given a dataset could find a synthetic sequence after sequencing an organism given the vast amount of natural noise in a typical dataset. The current path forward would typically be to first align and assemble a given dataset to a reference genome. For example, if yeast was being sequenced, then the short DNA transcripts acquired from sequencing would be compared to a yeast reference genome and then spliced together to form a picture of what the particular strain of yeast looks like. At that point, an expert could look at the genome to determine what did not fit. This could be accomplished by tracking the phylogeny of all of the genes that have been characterized and determining if they fit into the same evolutionary pathway as the yeast. For more subtle changes, historical mutation rates may be considered to try to determine the chance that the type of change observed in the yeast would have occurred naturally considering past evidence as a construct for the rate of change that is expected to be observed. While methods such as this (as there is no truly defined way of solving the problem) could get one closer to base truth, neither of these examples provides a complete solution. It is not sufficient to simply find a gene that does not fit into the evolutionary pathway of the organism and assume that the change came from genome editing as there are a variety of possible natural explanations, such as horizontal gene transfer, where the genomic material is passed between species. In the second example relating to detection of more subtle changes, there could have been an impetus such as high selection pressure that may explain why an organism may adjust more quickly to its environment than history would otherwise expect for completely natural changes. Additionally, there are typically instances in which some amount of DNA from a sequencing run cannot be aligned or assembled at all. These instances can result in situations where a synthetic sequence could otherwise be lost in this "noise" and would therefore not be subjected to the analysis described above. The power of the classifier 20, at least in part, may therefore lie in the fact that the classifier 20 does not simply look for attributable features that would constitute what traditional bioinformatics would define as features. Instead, the classifier 20 uses a data driven approach where algorithms are defined and improved for machine learning to determine what differentiating features show up in the data. Thus, example embodiments may not only operate more quickly, but can also operate to identify synthetic sequences which may otherwise be lost in the noise mentioned above due to their inability to be aligned or assembled.

The classifier 20 may therefore be employed to solve difficult problems in widely varying contexts with equally fast and accurate results. As an example, a particular problem may arise in which a new infectious agent is implicated in a rapidly spreading disease outbreak in one of the major economic centers of the country. It may be questioned as to whether the infectious agent is a natural occurrence or an intentional release of an engineered and highly specialized pathogen by a hostile power. Such a situation may require high quality and rapid answers in order to ensure that a proper and timely response to the outbreak is politically and medically enacted. To address the situation, the infectious agent may be captured, characterized and sequenced as per normal protocol. As part of the normal characterization, the sequenced sample (i.e., the raw sequenced data) may be run through the classifier 20 in order to initially determine whether the agent is of natural or synthetic origin. If the infectious agent is determined to be engineered, treatments may be altered to ensure that any treatment resistances are mitigated and the spread of the infectious agent may be significantly slowed or stopped. The information about the engineered sample may also be rapidly transferred to the intelligence community and, aided by a secondary classification layer of the classifier 20, attribution may be quickly assigned and a recommended path forward may be determined.

In another example, an illegal bioweapons program may be suspected in a hostile foreign nation. Given that there is no physical access to the facilities associated with the program, the only accessible materials associated with the program may be waste streams. The material from the waste streams may be sampled, but could be expected to be diluted in substantial background material. Thus, bioinformaticians would likely not be able to use any of the typical tools at their disposal to determine whether the program is indeed producing illegal bioweapons since you cannot assign a genomic fragment to any one organism within the mixture. Therefore, higher order analyses that are performed at the gene level on an organism are intractable. However, the classifier 20 may employ its advanced machine learning algorithms, which are able to search for genome editing marks directly, as opposed to determining the effects on the evolutionary pathways of an organism, in order to determine whether synthetic agents are being produced by the program. Many other use cases and scenarios are also imaginable.

Example embodiments may be expected to result in significant cost reductions depending upon the situations in which the classifier 20 is used. That said, if the classifier 20 is added to an existing DNA sequencing pipeline, the classifier 20 may provide additional scanning tools at the additional cost of the classifier 20. However, the additional cost also adds functionality not provided before, or that would only be provided using the laborious processes described above involving expert analysis, which are significantly more costly than the classifier 20, and take much more time without any assurance of better (or even comparable) accuracy. The classifier 20 does not involve the same costs in human intervention and curation, and therefore also involves less labor and computational time/resources as compared to the alternate tools mentioned above.

The ability of the classifier 20 to work at the read length scale of any commercial or future genome or DNA sequencer creates a huge advantage in terms of both time and accuracy. Given that genome sequencers are not designed to produce the entire sequence of an organism from position 1 to position n, the ability of sequencers to read much smaller pieces (e.g., as small as 75 bp or lower) in a massively parallel fashion fits quite well when married with the flexibility of the classifier 20. The classifier 20, which works at the read-length level of the sequencer, can save significant time and computational costs. Moreover, the classifier 20 has the flexibility to add additional modules to further classify sequences based on attributes or characteristics of various types. Thus, the classifier 20 can effectively work as a sorting mechanism to keep from performing the entire time consuming alignment process on all reads from the sequencer, which would otherwise be required. No alignment and/or assembly is required for the classifier 20 to operate. Moreover, the classifier 20 employs algorithms that work in conditions that are complex including on diluted samples or dirty samples where standard alignment and assembly procedures would otherwise be impossible. Additionally, the classifier 20 is generally not prone to false positive modalities and failure modes of captured natural processes such as horizontal gene transfer.

Figure 4:
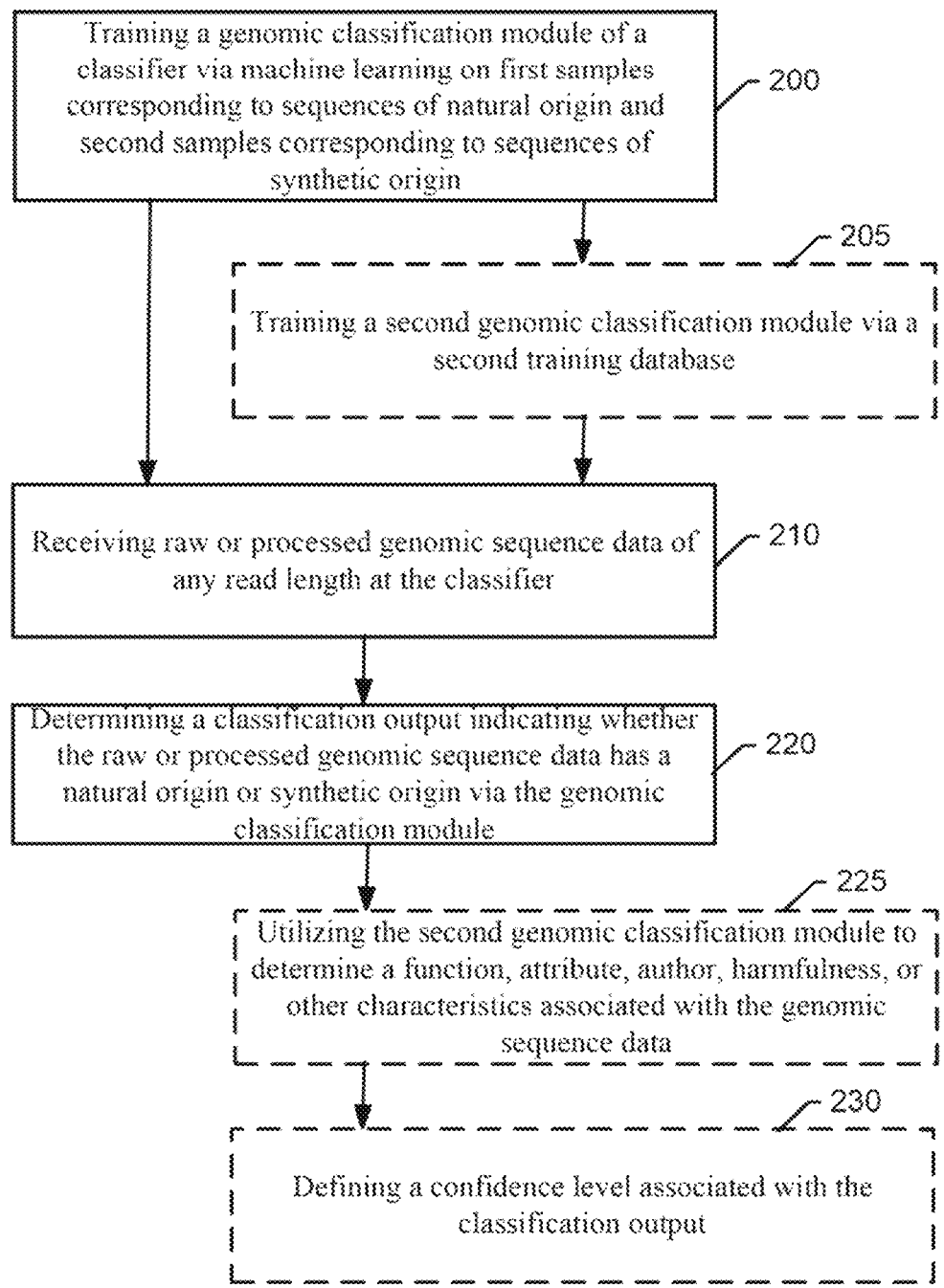
FIG. 4 illustrates a method of classifying an origin of genomic sequence data according to an example embodiment.

From a technical perspective, the classifier 20 described above may be used to support some or all of the operations described above. As such, the platforms described in FIGS. 1-3 may be used to facilitate the implementation of several computer program and/or network communication based interactions. As an example, FIG. 4 is a flowchart of a method and program product according to an example embodiment of the invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a user terminal (e.g., a computer, server, and/or the like) and executed by a processor in the user terminal. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method according to one embodiment of the invention is shown in FIG. 4. The method may include training a genomic classification module of a classifier via machine learning on first samples corresponding to sequences of natural origin and second samples corresponding to sequences of synthetic origin at operation 200. The method may further include receiving raw or processed genomic sequence data of any read length at the classifier at operation 210, and determining a classification output indicating whether the raw or processed genomic sequence data has a natural origin or synthetic origin via the genomic classification module at operation 220.

In an example embodiment, an apparatus for performing the method of FIG. 4 above may comprise a processor (e.g., the processor 52) or processing circuitry configured to perform some or each of the operations (200-220) described above. The processor may, for example, be configured to perform the operations (200-220) by performing hardware implemented logical functions, executing stored instructions, or executing algorithms for performing each of the operations. In some embodiments, the processor or processing circuitry may be further configured for additional operations or optional modifications to operations 200 to 220. Some examples of such additional operations are shown in dashed lines in FIG. 4. In this regard, for example, the method may further include training a second genomic classification module via a second training database at operation 205, and utilizing the second genomic classification module to determine a function, attribute, author, harmfulness, or other characteristics associated with the genomic sequence data at operation 225. Of note, operations 205 and 225 can be repeated for any number In some cases, the method may further include defining a confidence level associated with the classification output at operation 230.

An example of an optional modification may include a modification of training the genomic classification module such that it includes training a first neural network and a second neural network. In such an example, the first and second neural networks may each be optimized for operation over a respective different read length range. Alternatively or additionally, determining the classification may include providing an output of the first neural network, which comprises a convolutional neural network, as an input to the second neural network, which comprises a recurrent neural network. This is one example of combining an output from the first and second neural networks, and such combination may be used to determine the classification output.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A system for classifying an origin of genomic sequence data, the system comprising:

a training database comprising sample data including first samples corresponding to sequences of natural origin and second samples corresponding to sequences of synthetic origin; and a classifier comprising a genomic classification module, the genomic classification module trained via machine learning on the first and second samples, wherein the genomic classification module is configured to receive genomic sequence data of any read length and determine a classification output indicating whether the genomic sequence data has a natural origin or synthetic origin.

2. The system of claim 1, wherein the genomic classification module comprises a first neural network and a second neural network, the first and second neural networks each being optimized for operation over respective different read length ranges.

3. The system of claim 2, wherein the first neural network comprises a convolutional neural network and the second neural network comprises a recurrent neural network.

4. The system of claim 2, wherein an output of the first neural network is provided as an input to the second neural network.

5. The system of claim 4, wherein a combined output from the first and second neural networks is provided to a decision engine, and wherein the decision engine provides the classification output based on the combined output.

6. The system of claim 1, wherein the classifier is further comprises a second genomic classification module and a second training database, and wherein the second genomic classification module is configured, via the second training database, to determine an attribute of the genomic sequence data.

7. The system of claim 1, wherein the classifier is further comprises a second genomic classification module and a second training database, and wherein the second genomic classification module is configured, via the second training database, to determine a function associated with the genomic sequence data.

8. The system of claim 1, wherein the classifier is further comprises a second genomic classification module and a second training database, and wherein the second genomic classification module is configured, via the second training database, to determine an author of the genomic sequence data.

9. The system of claim 1, wherein the classifier is further comprises a second genomic classification module and a second training database, and wherein the second genomic classification module is configured, via the second training database, to determine harmfulness of the genomic sequence data.

10. The system of claim 1, wherein genomic classification module determines a function or functions to define a pathway between features of the first and second samples and a respective determination that the sequences are of natural origin or synthetic origin, and wherein the genomic classification module applies the function or functions to the genomic sequence data to determine whether the genomic sequence data is of natural origin or synthetic origin.

11. The system of claim 1, wherein the genomic classification module is further configured to define a confidence level associated with the classification output.

12. A method of determining an origin of genomic sequence data, the method comprising:

training a genomic classification module of a classifier via machine learning on first samples corresponding to sequences of natural origin and second samples corresponding to sequences of synthetic origin;

receiving raw or processed genomic sequence data of any read length at the classifier; and determining a classification output indicating whether the raw or processed genomic sequence data has a natural origin or synthetic origin via the genomic classification module.

13. The method of claim 12, wherein training the genomic classification module comprises training a first neural network and a second neural network, the first and second neural networks each being optimized for operation over respective different read length ranges.

14. The method of claim 13, wherein determining the classification comprises providing an output of the first neural network, which comprises a convolutional neural network, as an input to the second neural network, which comprises a recurrent neural network.

15. The method of claim 14, further comprising combining an output from the first and second neural networks to determine the classification output.

16. The method of claim 12, further comprising training a second genomic classification module and a second training database, and utilizing the second genomic classification module to determine an attribute of the genomic sequence data.

17. The method of claim 12, further comprising training a second genomic classification module and a second training database, and utilizing the second genomic classification module to determine a function associated with the genomic sequence data.

18. The method of claim 12, further comprising training a second genomic classification module and a second training database, and utilizing the second genomic classification module to determine an author of the genomic sequence data.

19. The method of claim 12, further comprising training a second genomic classification module and a second training database, and utilizing the second genomic classification module to determine harmfulness of the genomic sequence data.

20. The method of claim 12, further comprising defining a confidence level associated with the classification output.

* * * * *